United States Patent [19]
Coffman

[11] Patent Number: 5,148,454
[45] Date of Patent: Sep. 15, 1992

[54] APPARATUS FOR CONDUCTING CRANIAL X-RAY TOMOGRAPHY AND RADIOGRAPHY

[76] Inventor: George W. Coffman, 12307 Rip Van Winkle, Houston, Tex. 77024-4945

[21] Appl. No.: 750,510

[22] Filed: Aug. 27, 1991

[51] Int. Cl.[5] .............................................. A61B 6/14
[52] U.S. Cl. ...................................... 378/40; 378/38; 378/196
[58] Field of Search ..................... 378/38, 39, 40, 196, 378/197, 27

[56] References Cited

U.S. PATENT DOCUMENTS

| | | | |
|---|---|---|---|
| 4,017,737 | 4/1977 | Hudson | 378/39 |
| 4,653,083 | 3/1987 | Rossi | 378/197 |
| 4,741,015 | 4/1988 | Charrier | 378/197 |
| 4,868,845 | 9/1989 | Koropp | 378/197 |
| 4,974,243 | 11/1990 | McArdle | 378/39 |

*Primary Examiner*—Craig E. Church
*Attorney, Agent, or Firm*—James L. Jackson

[57] ABSTRACT

Apparatus according to the present invention is provided for conducting cranial X-ray tomography and radiography of human subjects and includes a horizontally oriented, motor driven rotatable shaft for imparting controlled rotation to an elongate support member having an X-ray source and film holder provided at opposed end portions thereof. The apparatus includes a cephalometer which supports the head of the subject at a fixed position during X-ray tomography and radiography procedures. The horizontal rotary shaft of the apparatus is controllably movable laterally, preferably horizontally, between successive X-ray exposures to achieve successive tomographic images on the X-ray film representing sections or cuts of the cranial site of interest.

27 Claims, 3 Drawing Sheets

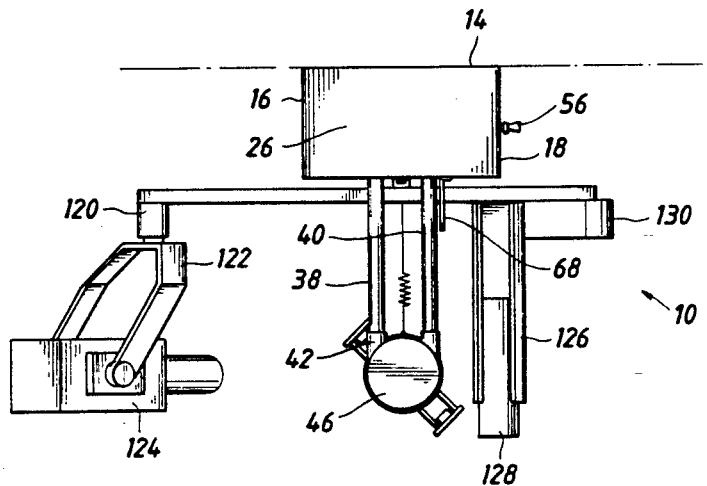
FIG. 3
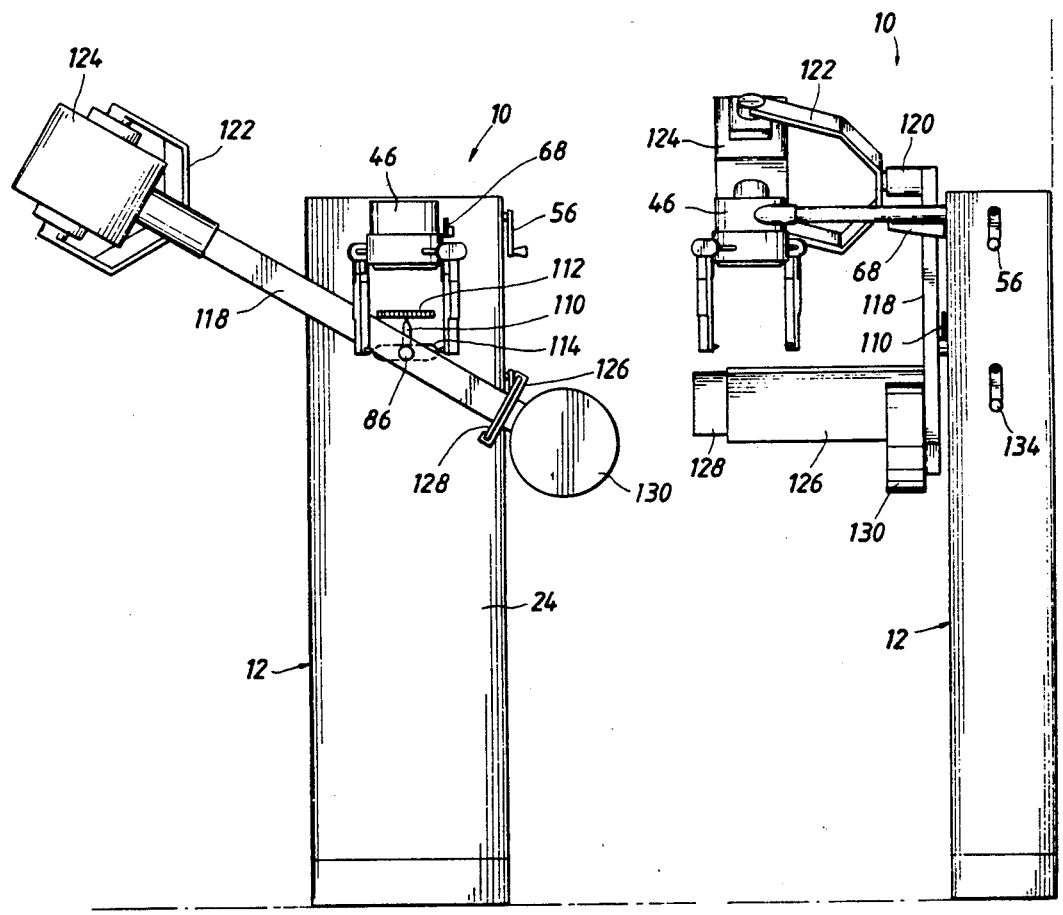
FIG. 1
FIG. 2

APPARATUS FOR CONDUCTING CRANIAL X-RAY TOMOGRAPHY AND RADIOGRAPHY

FIELD OF THE INVENTION

This invention relates generally to cranial X-ray tomography and radiography and more specifically is directed to X-ray tomographic apparatus defining "X" and "Y" axes with the Y axis being maintained fixed during cranial X-ray tomography and radiography while the X axis is capable of lateral incremental movement between successive X-ray exposures to thereby achieve multiple, X-ray images representing spaced X-ray cuts of a cranial anatomical site of interest.

BACKGROUND OF THE INVENTION

X-ray tomographic apparatus has been marketed for many years for the purpose of conducting X-ray cranial tomography to obtain plural, evenly spaced X-ray cuts of a cranial site of interest such as the temporo-mandibular joint for example. In every case tomographic apparatus is positioned such that an X-ray head and an X-ray film cassette are positioned on opposite sides of the patient's anatomical site of interest. The X-ray head and film cassette are movable about the anatomical site of interest while the X-ray head is energized to achieve each tomographic image on the film such as being supported on a pivotally movable arm that is rotated about a pivot point. This pivotal motion blurs out all anatomy in front of and behind the pivot point and thus provides an X-ray exposure that is representative of a section taken through the anatomical site of interest. In many cases, depending upon the character of X-ray tomograph that is desired, the apparatus accomplishing rotary movement of the X-ray head and film holder will move either the X-ray head or film holder or both along an elliptical path such as substantially conforming to the configuration of the mandibular of the patient. This type of apparatus is widely utilized in dentistry and for maxillo-facial surgery although it has a number of other uses as well.

For the most part, the X-ray tomography apparatus that has been developed and marketed accomplishes rotation of the X-ray head and film support arm about a substantially vertical axis so that the arcuate movement of these components is in a substantially horizontal plane. U.S. Pat. Nos. 4,675,888 of Gastrin; 4,823,369 of Guenther, et al.; and 4,852,134 of Kinanen, et al. are representative of simple vertical axis rotation of an arm that supports the X-ray head and film holder. More complex rotary movement of a support for an X-ray head and film holder, including relative lateral movement during rotation is evidenced by U.S. Pat. Nos. 4,741,007 of Virta, et al.; 4,756,014 of Doebert; 4,783,793 of Virta, et al.; 4,811,372 of Doebert, et al.; 4,813,060 of Heubeck, et al.; 4,856,038 of Guenther, et al.; 4,907,251 of Mork, et al.; and 4,985,907 of Moteni. Although each of the U.S. Patents previously identified describe rotation of a support for an X-ray head and film holder about a vertical axis, one patent, namely U.S. Pat. No. 4,974,243 of McArdle, et al. discloses a positioning system for X-ray tomography including an X-ray head and film support arm or spar that rotates about a fixed horizontally oriented axis with respect to the '243 patent of McArdle, et al., it should be noted that the head fixator mechanism 50 includes an associated X, Y and Z positioning mechanism 52, thus, the head fixator or cephalostat is positionable utilizing X, Y and Z translational mechanisms representing adjustment in each of X, Y and Z cartesian coordinates.

Although X-ray tomography systems such as that shown by the '243 patent of McArdle, et al. are quite functional, nevertheless, they are for the most part of quite complicated design and function and therefore are quite expensive from the standpoint of purchase, installation and repair. It is desirable to provide X-ray tomography apparatus having characteristics of low cost, simplicity and yet being efficient from the standpoint of functionality.

SUMMARY OF THE INVENTION

It is a primary feature of the present invention to provide novel method and apparatus for cranial X-ray tomography and the like through use of an X-ray tomography system that permits the cranial anatomy of a human subject to remain fixed during multiple spaced tomographic X-ray exposures.

It is another feature of the present invention to provide novel X-ray tomographic apparatus incorporating a support for an X-ray head and film holder is pivotal about a horizontal axis and wherein the horizontal axis is capable of incremental, lateral movement between successive X-ray exposures to yield successive spaced X-ray cuts of the cranial anatomical site of interest.

Even further, it is a feature of this invention to provide a mechanism for controlling equally spaced lateral positioning of a horizontally oriented axis for an X-ray source and film holder support to enable efficient, accurate use of the apparatus for achieving accurate multiple, evenly spaced X-ray cuts of a cranial anatomical site of interest.

Other and further features of the present invention which will become apparent upon a complete understanding of the present invention, are considered to be within the spirit and scope of this invention.

Briefly, X-ray tomographic apparatus constructed in accordance with the present invention includes a housing structure such as might rest on the floor of a dental operatory or the like. Alternatively, the housing structure may be wall supported if desired. From the housing, there is projected a lateral support structure for a cephalostat having the capability of establishing fixing engagement with the head of the patient so as to station an anatomical site of interest, such as the temporo-mandibular joint, for example, at a fixed location during multiple X-ray tomographic exposures. The cephalostat is a commercially available mechanism such as is manufactured and sold by Wehmer Corporation of Franklin Park, Illinois. The cephalostat includes a pair of ear post support arms depending therefrom that are movable by an internal mechanism toward or away from one another. These arms are provided with ear posts that engage the meatus at the auditory canal of the cranial anatomy to achieve fixation of the head of the patient at a specific spatial location for X-ray tomography of the anatomical site of interest. The cephalostat may also be provided with other cranial engagement apparatus to enhance stabilization of the patient's head at a fixed location. The cephalostat is adjustable according to the teachings of the present invention only from the standpoint of rotation of the ear post support arms about a vertical axis such as for angular positioning of the patient's head and from the standpoint of spatial positioning of the cephalostat in relation to the housing. This spatial positioning of the cephalostat achieves appropriate positioning of a patient at a location relative to a narrow angle X-ray beam projected from the X-ray source to X-ray film being supported by the film cassette.

Internal apparatus of the housing provides rotatable support for a horizontally oriented shaft having an elongate X-ray source and cassette support arm or beam fixed intermediate its extremities thereto. At or near one end of the support beam positioned supported an X-ray source of conventional nature having the capability of projecting a narrow angle beam of X radiation to an X-ray film cassette supported near the opposite extremity of the arm. Shaft and beam rotating means is also provided within the housing structure and accomplishes controlled rotation of the shaft and the support beam attached thereto during a tomographic X-ray exposure. The support beam, together with the X-ray source and X-ray film holder comprise an imaging assembly which is rotatable about the horizontal shaft during tomographic imaging. The patient is positioned by the cephalostat with the anatomical site of interest specifically located to be intersected by the narrow beam of X radiation to form an image on the X-ray film that is representative of a section taken through the anatomical site of interest. The patient will be located with the anatomical site of interest positioned precisely at the longitudinal axis of the rotatable shaft which is also precisely at the X-cartesian axis. As discussed above, rotation of the support arm during X-ray exposure of the film causes all anatomy on either side of the X-axis defined by the longitudinal axis of the rotary shaft to be blurred and thus the resulting image on the X-ray film is representative of a section or cut taken through the anatomical site of interest as is typically the case with cranial tomography.

Within the housing structure is provided means for accomplishing controlled lateral positioning of the horizontally oriented shaft between successive X-ray tomographic cuts. Initiation of X-ray tomography occurs with the horizontally oriented rotary shaft located in preselected relation with the anatomical site of interest. After each X-ray exposure, the horizontal shaft is moved laterally, i.e., horizontally, a desired increment of movement. By moving the horizontal shaft laterally or horizontally between successive X-ray exposures, there is provided on the X-ray film of the film cassette a plurality of successive X-ray exposures each representing a section taken through the anatomical site of interest. By comparison of these X-ray sections, a doctor experienced in X-ray tomography, is enabled to make structural determination of the anatomy of the patient at the site of interest. In the event abnormalities are diagnosed, appropriate remedial procedures can be carried out. The patient's head, from the first X-ray cut to the last, is maintained at a fixed location by the apparatus. These features taken in combination permit the manufacture and use of apparatus that is of simple and reliable nature and is low in cost and yet is capable of providing quality X-ray tomography of a cranial anatomical site of interest or the like.

BRIEF DESCRIPTION OF THE DRAWINGS

So that the manner in which the above recited features, advantages and objects of the present invention are attained and can be understood in detail, a more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

In the Drawings

FIG. 1 is an elevational view of apparatus for X-ray tomography that is constructed in accordance with the teachings of the present invention.

FIG. 2 is a side elevational view of the X-ray tomographic apparatus of FIG. 1.

FIG. 3 is a plan view of the X-ray tomographic apparatus of FIGS. 1 and 2.

FIG. 4 is a partial elevational view of the X-ray tomographic apparatus of FIGS. 1-3 showing the upper portion of the housing structure with the front wall thereof removed and with portions thereof illustrated in sections.

FIG. 5 is a sectional view taken along line 5—5 of FIG. 4.

FIG. 6 is a sectional view taken along line 6—6 of FIG. 5 and showing a bottom view of apparatus for supporting guiding and positioning the cephalostat.

FIG. 7 is a partial elevational view of an intermediate portion of the housing structure with the front wall thereof being removed and illustrating the shaft support and positioning mechanism thereof in detail.

FIG. 8 is a sectional view taken along line 8—8 of FIG. 7.

FIG. 9 is a sectional view taken along 9—9 of FIG. 7.

DETAILED DESCRIPTION OF PREFERRED EMBODIMENT

Figure 4:
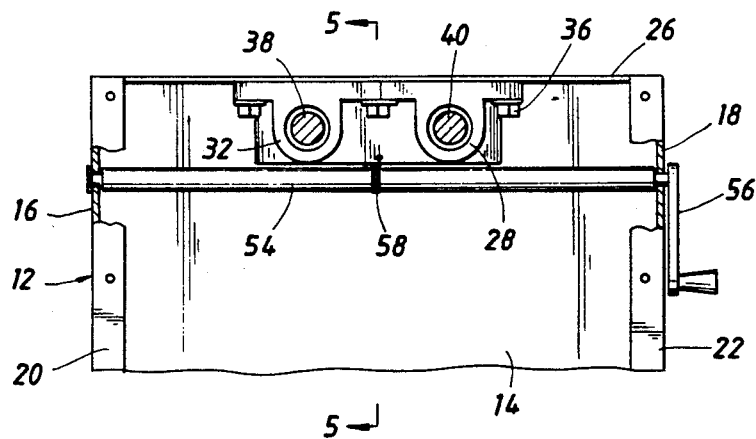

Referring now to the drawings and first to FIGS. 1, 2 and 3, apparatus for conducting cranial X-ray tomography and radiography of human subjects is illustrated generally at 10 and incorporates a housing structure 12 which may be a housing capable of having its lower end resting on the floor 14 of a dental operatory as shown in FIGS. 1 and 2 or, in the alternative, the housing may be of limited height and may be adapted to be supported by the wall structure of the dental or surgical operatory depending upon the needs and desires of the user.

The housing 12 defines a rear wall 14 and opposed side walls 16 and 18 with each side wall defining panel support flanges 20 and 22 that provide for support of a front panel 24 which is connected to the support flanges by means of screws, bolts, or the like.

Figure 5:
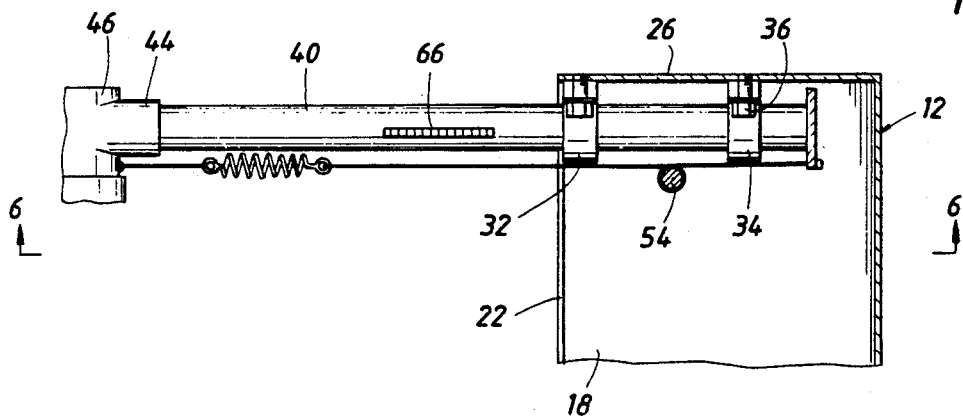
Figure 6:
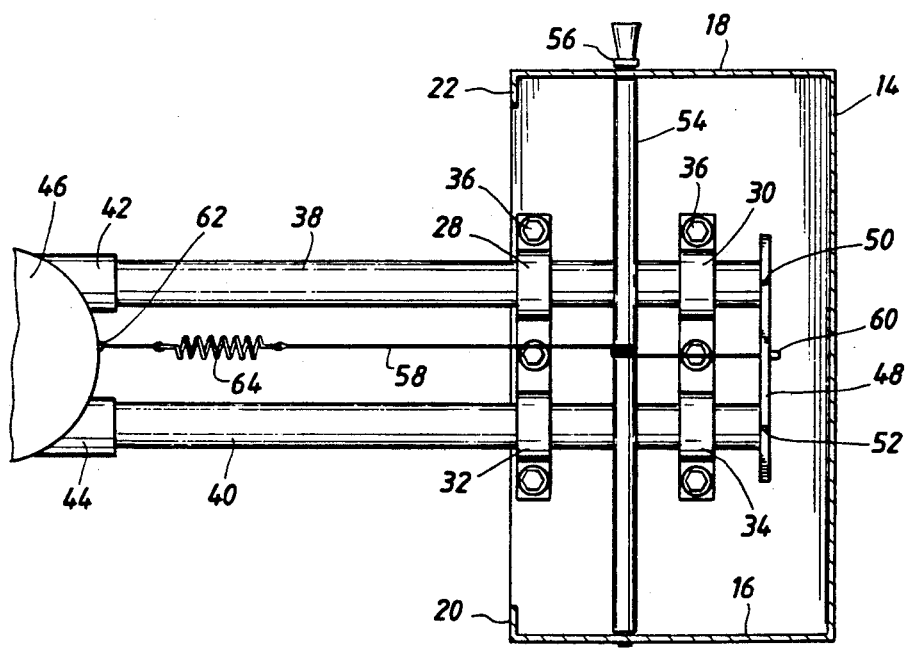

As shown in FIGS. 4 and 5, the housing structure 12 is also provided with an upper wall 26 having cephalostat guide means supported thereby. As shown in FIGS. 4-6 the cephalostat guide means comprise two pairs of guide bushings, one pair being aligned guide bushings 28 and 30 and the other pair being aligned guide bushings 32 and 34. The guide bushings 28-34 are supported by a plurality of bolts 36 that are received by appropriate thread apertures defined by the top wall 26. A pair of elongate cephalostat guide members 38 and 40 are received in guided relation by respective pairs of the guide bushings and are connected at the outer extremities thereof to connector elements 42 and 44 respectively of the cephalostat 46.

It is desirable to achieve controlled positioning of the cephalostat 46 so that the patient's anatomical site of interest can be brought into precise registry with the narrow beam of X-radiation that is emitted from the X-ray source. Thus precise positioning of the cephalostat support bars 38 and 40 is necessary. To achieve such activity at their respective inner extremities, the support bars 38 and 40 are connected to a transverse actuator connector plate 48 by means of set screws 50 and 52. A cephalostat positioning shaft 54 is rotatably supported by the side walls 16 and 18 of the housing and is manually rotatable by means of a crank 56. A cephalostat drive cable 58 is provided with one end 60 thereof being connected to the actuator connection plate 48.

As is evident from FIG. 6, several loops of the drive cable 58 are wrapped about the cephalostat actuator shaft. The drive cable 58 is connected at 62 to the cephalostat 46 and is provided with an intermediate tensioning spring 64 that maintains the cable taut so that an efficient frictional driving relationship is established between the actuator shaft 54 and the cable. Thus, upon rotation of the crank 56 by manual force, the cephalostat actuator cable 54 is directly located and its frictional engagement with the cable 58 induces driving force to the cable for inward or outward positioning of the cephalostat bars relative to the housing 12. Positioning indica 66 is provided on at least one of the support bars so that its position can be visually determined by visual comparison thereof to a pointer 68 that projects forwardly from the front wall 24 of the housing.

Figure 7:
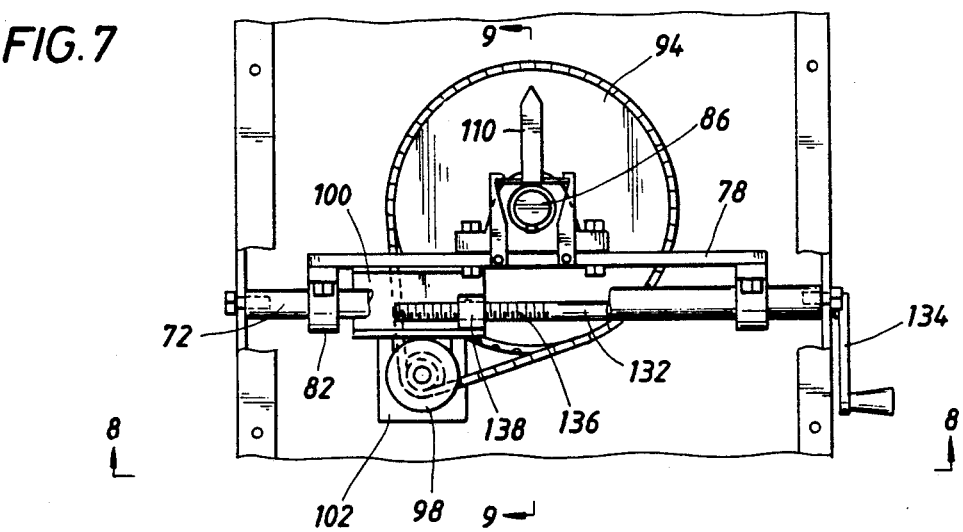
Figure 8:
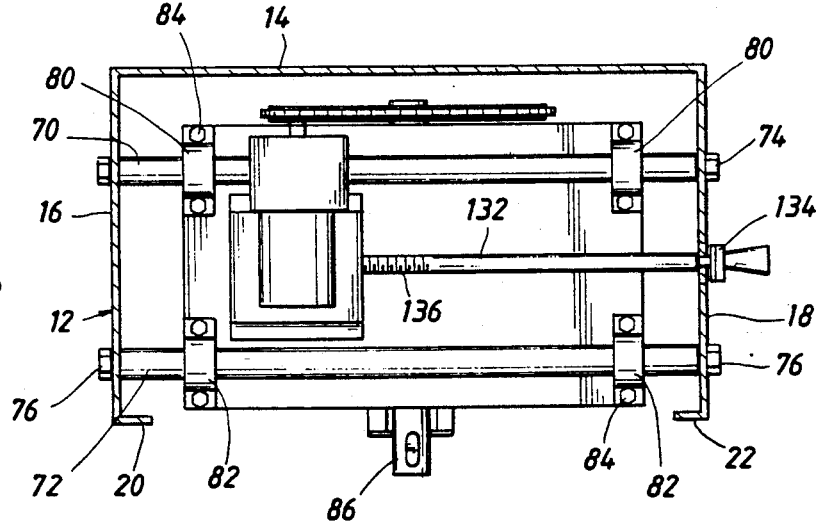
Figure 9:
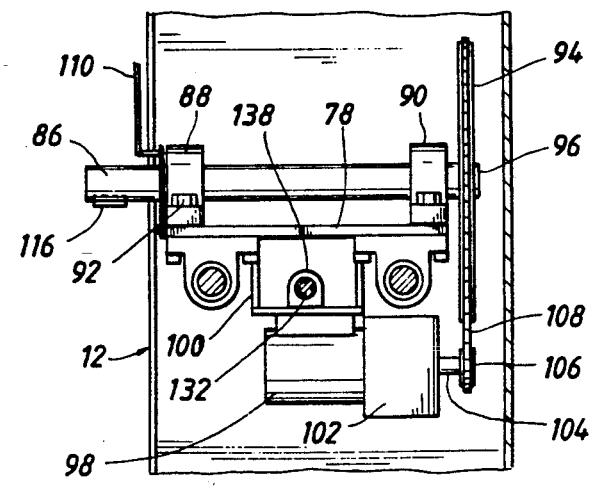

Referring now particularly to FIGS. 7, 8 and 9, it is desirable to provide means for supporting a rotary shaft in generally horizontal manner and to impart control lateral positioning of the rotary shaft, typically in a horizontal plane, in order to provide for controlled positioning of an X-ray source and film holder at each tomographic cut or film exposure while the head of the patient is maintained static during the entire procedure. Apparatus accomplishing this desirable feature may conveniently take the form illustrated, particularly in FIGS. 7, 8 and 9 where a pair of elongate guide bars 70 and 72 are shown particularly in FIG. 8 to be secured in fixed location relative to the housing by means of respective pairs of connector bolts 74 and 76. A shaft support platform 78 is movably positioned within the housing for controlled linear movement, being supported within the housing by means of respective pairs of aligned guide bushings 80 and 82 which are secured to the bottom of the shaft support platform 78 by means of a plurality of bolts 84 or other suitable connector devices. Thus, the guide shafts 70 and 72 restrict the shaft support platform 78 to linear lateral movement within the housing.

As is evident from FIGS. 7 and 9, a rotary shaft 86 is supported for rotation relative to the shaft support platform 78 by an aligned pair of pillow blocks or bushings 88 and 90 that are connected by bolts 92 to the shaft support platform. Thus, the axis of rotation of the rotary shaft 86 is fixed with respect to the shaft support platform 78 but the shaft support platform is laterally movable; consequently, the shaft 86 is both rotary and laterally movable relative to the housing structure. It is necessary to impart controlled rotation to the shaft 86 and to impart lateral positioning of the shaft. These features are accomplished according to the teachings of the present invention by an exemplary shaft rotating and positioning mechanism according to the preferred embodiment of the present invention. It is to be born in mind, however, that other shaft rotation and lateral positioning mechanisms may be employed without departing on the spirit and scope of the present invention.

According to the teachings of the present invention the shaft rotating and position controlling mechanism may conveniently comprise a driven sprocket 94 which is connected in non-rotatable relation to the inner end portion 96 of the shaft. A reversible electric motor 98 is fixed by a structural member 100 to the lower surface portion of the shaft support platform 78 such as by means of bolting, welding, or the like and includes a reduction gear assembly 102 having its internal gearing connected to the output shaft of the motor. The reduction gear 102 has a rotary output shaft 104 to which is non-rotatably connected a drive sprocket 106. The drive sprocket 106 and the driven sprocket 94 receive a drive chain 108 in driving relation therewith. Consequently, upon rotation of the output shaft 104, the chain and sprocket mechanism imparts rotary movement to the driven sprocket 94 and to the rotary shaft 86.

It is appropriate to visually identify the lateral position of the rotatable shaft 86 relative to the housing structure 12. This feature is accomplished by a position indicating pointer 110 that is supported in fixed relation with the shaft support platform 78 and is thus laterally movable along with the rotatable shaft 86. As shown in FIG. 1, the pointer 110 is registerable with indica 112 that is located on the front surface of the front wall 24 of the housing structure. The indica 112 is typically a measuring device measuring in millimeters either side of a zero position but it can be of other suitable form within the spirit and scope of this invention. The front wall 24 of the housing is provided with an elongate generally horizontally disposed opening 114, a part of which is shown in broken lines in FIG. 1 so as to permit relative lateral movement of the rotatable shaft 86 which projects through the lateral opening to a position forwardly of the front wall panel 24.

It should be born in mind that the longitudinal axis of the rotatable shaft 86 defines an X-axis while the laterally movable support for the cephalostat 46 defines a Y axis. Since neither the rotatable shaft 86 nor the cephalostat 46 are vertically adjustable, the apparatus does not include a Z axis. Obviously, from the standpoint of the present invention, a Z axis of adjustment is not necessary because the head of the patient is maintained at a fixed position throughout the multiple exposure X-ray tomographic procedure.

The outer portion of the rotary shaft 86 is provided with a keyway and key 116 with the key being received within an appropriate keyway defined in a connection aperture of an elongate pivotal support member 118 such that the connection aperture is located intermediate the extremities of the elongate support member. At one end of the support member is provided a support 120 including a support bracket 122 for support of an X-ray head 124. The X-ray head is of the character for emitting a very narrow beam of X-radiation that is suitable for X-ray tomography. Adjacent the opposite end of the elongate support member 118 is provided a film cassette holder 126 which provides support for an X-ray film cassette 128. Because of the relative positions of the X-ray source 124 and the X-ray film cassette 128, to properly balance the elongate support element 118 relative to the rotary shaft 86, a counterweight 130 may be secured to the free extremity of the support member near the film cassette holder 126. Thus, as the rotary shaft 86 is moved laterally, the pivotal position of the support arm is also moved laterally, this lateral movement being indicated by the relationship of the pointer 110 with the indica 112. The support element or beam 118, together with the X-ray source and film holder and the horizontally oriented rotary shaft constitute an imaging assembly that is shifted laterally, preferably horizontally following each tomographic X-ray exposure, thus forming on X-ray film, a plurality of tomographic images representing adjacent cross-sections through the anatomical site of interest.

It is appropriate within the scope of this invention to induce lateral, typically horizontal movement to the rotatable shaft 86 between successive X-ray cuts. One suitable mechanism for accomplishing this feature may conveniently take the form illustrated particularly in FIGS. 7, 8 and 9 where an actuator shaft 132 is shown with the outer end thereof supported for rotation by one of the side walls 18 of the housing structure. A crank member 134 is fixed in non-rotatable rotation to the outer extremity of the actuator shaft. The internal end of the actuator shaft is provided with external threads as shown at 136 with these threads being disposed in threaded engagement with internal threads formed within an actuator projection 138 as shown in FIGS. 7 and 9. Thus, upon rotation of the actuator shaft 132, the connector projection 138 which functions as a drive nut, imparts lateral force to the motor support 100 and to the shaft support platform 78 for lateral movement of the platform and thus the rotatable shaft. The external threads 136 will determine the length of lateral movement that occurs upon each rotation of the actuator shaft. The threads 136 will thus be designed to induce a desired increment of lateral movement to the shaft support platform upon each rotation of the crank 134. This lateral movement may be determined as best suits the needs of those conducting X-ray tomographic activities.

OPERATION

Use of the apparatus set forth in the drawings and explained hereinabove, is initiated by positioning of the anatomical site of interest of the patient, i.e., the TMJ, at a specific location with respect to the "X" axis which is defined by the longitudinal axis of the rotary horizontally oriented shaft 86. Positioning of the head of the patient in this manner is accomplished by adjusting the depending arms of the cephalostat 46 such that the ear posts come into proper contact with the meatus at the auditory canal of the patient. With the patient's head properly stabilized by the cephalostat, with the patient standing or preferably seated and with the patient properly oriented as suits the needs of the dentist or doctor, the cephalostat adjustment crank 56 is rotated in an appropriate direction for driving the actuator shaft 54 and through the frictional driving relationship of the shaft with the cable 58 imparting linear movement to the actuator plate 48 and the sublometer support bars 38 and 40. This activity accomplishes movement of the head of the patient inwardly or outwardly to precisely position the anatomical site of interest with respect to the narrow beam of X-radiation that will be emitted from the X-ray head. Tomographic exposure is then begun with the pointer 110, which identifies lateral positioning of the rotary shaft 86 and the support arm 118 identifying a predetermined starting position for a series of X-ray cuts at spaced intervals. This is accomplished by positioning the pointer 110 in registry with a selected reference of the indica 112.

With the patient secured stationary by the cephalometer 46, the X-ray head 124 is energized causing a narrow beam of X-radiation to be directed through the "X" axis to the film cassette 128. Simultaneous with energization of the X-ray source 124, the drive motor 98 is also energized to induce rotation of the shaft 86 and arm 118 by actuation of the drive mechanism including the reduction gear 102, output shaft 104 and the chain and sprocket drive mechanism. The shaft 86 is rotated, causing the arm 118 to pivot in a vertical plane located in normal relation to the rotary shaft 86. The arm 118 is pivoted by the horizontal shaft through a prescribed included angle of movement while the X-ray source is energized so that a tomographic exposure will occur on the film with all anatomy either side of the "X" axis being blurred and thus causing a sharp X-ray exposure to appear on the film which represents a section taken through the anatomical site of interest.

After the support arm 118 has completed its angular movement with the X-ray source energized, the X-ray source will be deenergized and angular movement of the support arm will be reversed by a reversal of its drive shaft rotation, causing the support arm to return to its initial position. To determine the limits of angular movement of the support arm, any suitable control mechanism may be employed within the spirit and scope of the present invention. For example, electrical control circuits employing limit switches may be incorporated within the mechanism to stop angular arm movement at the desired limits of support arm travel.

After the support arm has completed its return travel, being driven by reverse rotation of the rotary horizontally oriented shaft 86, or during return travel thereof, the rotary shaft adjustment crank 134 may be rotated one or more revolutions as desired, causing the threaded engagement of the actuator shaft 132 with the internal threads of the connector projection 138 to impart precise lateral movement to the shaft support platform 78 and its components, including the horizontal rotary shaft. Obviously lateral movement of the rotary shaft 86 causes lateral positioning of the support arm, X-ray head and film cassette. Typically the shaft 134 will be rotated one revolution and the threads 136 will be designed to provide a predetermined increment of lateral shaft movement, i.e., one millimeter for example. After this has been done, the apparatus is then at its initial position having completed one cycle of operation and being ready to take another X-ray cut that is offset a predetermined distance from the previous X-ray cut. As is typical with X-ray tomographic apparatus, the position of the film cassette is adjusted after each X-ray exposure. The tomograph is energized through a number of successive cycles as indicated above, with the horizontally oriented axis 86, i.e., "X-axis", being moved laterally or horizontally one increment of movement between each X-ray film exposure and accomplishing consequent lateral positioning of the areas of movement of the X-ray head and film cassette relative to the fixed anatomical site of interest. At the conclusion of the desired number of X-ray tomographic cycles, the X-ray film will be exposed in a manner representing a number of successive X-ray cuts taken through the anatomical site of interest. According to the teachings of the present invention, the horizontally oriented shaft 86, representing the X-axis is moved laterally, typically horizontally to accomplish each X-ray cut, with the anatomical site of interest being fixed at a predetermined location from the first X-ray cut to the last.

In view of the foregoing, it is evident that the present invention is one well adapted to attain all of the objects and features hereinabove set forth, together with other objects and features which are inherent in the apparatus disclosed herein.

As will be readily apparent to those skilled in the art, the present invention may be produced in other specific forms without departing from its spirit or essential characteristics. The present embodiment, is therefore, to be considered as illustrative and not restrictive, the scope of the invention being indicated by the claims rather than the foregoing description, and all changes which come within the meaning and range of the equivalence of the claims are therefore intended to be embraced therein.

What is claimed is:

1. A method for cranial X-ray tomography and radiography that is accomplished through utilization of an imaging assembly including an X-ray source and X-ray film holder that are disposed in spaced, opposed relation, said imaging assembly being fixedly supported by a substantially horizontal, rotatable and laterally movable shaft projecting from a housing and thus being rotatable by said shaft about a generally horizontal axis located intermediate said X-ray source and X-ray film holder such that X-ray film of said X-ray film holder is intersected by the beam of radiation emitted by said X-ray source, said method comprising:

(a) positioning a cranial anatomical site of interest at a fixed location with respect to an "X" cartesian axis such that upon energization of said x-ray source, a beam of radiation from said X-ray source is projected through said cranial anatomical site of interest and said "x" axis to said X-ray film;

(b) controllably rotating said shaft and said imaging assembly fixedly supported thereby about said generally horizontal axis while said X-ray source is energized, thus obtaining an X-ray exposure on said X-ray film representing a tomographic section of said cranial anatomical site of interest; and (c) selectively moving said shaft and thus said generally horizontal axis laterally between successive X-ray exposures of said X-ray film, while said cranial anatomical site of interest is maintained at said fixed location, whereby multiple X-ray tomographic images are obtained, each image representing a different tomographic section of said cranial anatomical site of interest.

2. The method of claim 1, wherein:
    said selective moving of said shaft and thus said X-axis is achieved incrementally between successive X-ray exposures of said X-ray film such that each of said tomographic images representing sections of said cranial anatomical site of interest represents a successive incremental tomographic section of the cranial anatomy of the patient.

3. The method of claim 1, wherein said X-ray source and X-ray film holder are supported in said spaced relation by an elongate support element being fixed intermediate the extremities thereof to said shaft defining said X-axis, said shaft supporting and imparts pivotal driving movement to said elongate support element, said method including:
    moving said rotatable and laterally movable shaft and thus said X-axis laterally following each tomographic exposure of said X-ray film.

4. The method of claim 3, including:
    moving said shaft horizontally following each tomographic exposure of said X-ray film.

5. The method of claim 3, including:
    moving said shaft substantially horizontally by a predetermined distance following each tomographic exposure of said X-ray film such that said images on said X-ray film represent successive equally spaced sections of said cranial anatomical site of interest.

6. The method of claim 1 wherein a mechanical shaft drive mechanism is provided for lateral positioning of said horizontal, rotatable and laterally movable shaft and said method includes:
    controllably operating said mechanical shaft drive mechanism between each tomographic X-ray exposure such that said horizontal, rotatable and laterally movable shaft is shifted horizontally by a predetermined increment of horizontal movement.

7. The method of claim 1 wherein said X-axis is defined by said shaft, said shaft providing support and rotational control for a support beam having said X-ray source and X-ray film holder mounted at spaced locations thereon, said method including:

(a) imparting controlled driving rotation to said shaft in one rotational direction from a starting position to an ending position with said X-ray source energized, thus pivoting said support beam and said X-ray source and film holder through a predetermined included angle of movement for tomographic exposure of said X-ray film;

(b) imparting controlled driving rotation to said shaft in the opposite rotational direction from said ending position to said starting position thus completing one cycle of tomographic movement of said support beam together with said X-ray source and said X-ray film holder; and (c) energizing said X-ray source during at least a portion of said cycle of tomographic movement for tomographic exposure of said X-ray film.

8. The method of claim 7, including:
    energizing said X-ray head only during controlled driving rotation of said shaft in said one rotational direction.

9. The method of claim 7, including:
    energizing said X-ray head only during controlled driving rotation of said shaft in said opposite rotational direction.

10. A method of X-ray cranial tomography and radiography through utilization of an X-ray tomograph having a cranial fixing mechanism, an imaging assembly including an X-ray source and film holder disposed in spaced relation and being fixedly supported by a substantially horizontally oriented, rotatable and laterally movable shaft and thus being pivotal by said shaft about a horizontal axis, said X-ray tomograph having means for controllably rotating said shaft thus pivoting said imaging assembly and energizing said X-ray source for tomographic exposure of X-ray film, said method comprising:

(a) positioning a patient with the cranial site of interest thereof located at the focal point of said X-ray source and maintaining the position of the patient static during a cranial X-ray tomographic procedure during which multiple X-ray tomographic images are formed on said X-ray film;

(b) rotating said shaft and thus said imaging assembly from a starting position in one rotational direction about said generally horizontal axis while said X-ray source is energized, thus forming a tomographic image on said X-ray film representing a section of said cranial site of interest;

(c) rotating said said shaft and thus imaging assembly in the opposite rotational direction with said X-ray source deenergized, thus returning said shaft and said imaging assembly to said starting position and thus completing a cycle of tomographic operation;

(d) incrementally shifting said shaft and thus said horizontally oriented axis laterally following each cycle of tomographic operation; and (e) operating said tomograph through multiple cycles of tomographic operation to thus form multiple X-ray images on said X-ray film each representing a different tomographic section through said cranial site of interest.

11. The method of claim 10, wherein a mechanical shaft drive mechanism is provided for lateral positioning of said substantially horizontally oriented, rotatable and laterally movable shaft, said method including:

controllably operating said mechanical shaft drive mechanism between each tomographic X-ray exposure of said film such that said substantially horizontally oriented, rotatable and laterally movable shaft is shifted horizontally by a predetermined increment of horizontal movement to thus form consecutive tomographic images on said X-ray film representing successive cross-sections of said anatomical site of interest.

12. The method of claim 10, including:

moving said substantially horizontally oriented, rotatable and laterally movable shaft substantially horizontal by a predetermined increment of horizontal movement following each tomographic exposure of said X-ray film such that images on said X-ray film represent successive equally spaced sections of said cranial anatomical site of interest.

13. The method of claim 10, including:

moving said substantially horizontally oriented, rotatable and laterally movable shaft horizontally following each tomographic exposure of said X-ray film.

14. Apparatus for conducting cranial X-ray tomography and radiography of human subjects, comprising:

(a) a support housing adapted for fixed positioning within a tomographic X-ray facility;

(b) a substantially horizontally oriented, rotatable and laterally movable shaft projecting from said support housing and defining an X-axis;

(c) means for controllably rotating said horizontally oriented shaft;

(d) an elongate support beam being fixed intermediate its extremities to said horizontally oriented shaft and being rotatable thereby;

(e) an X-ray source being supported at one end of said elongate support beam;

(f) an X-ray film holder being supported at the opposite end of said elongate support beam;

(g) means for substantially fixing the head of a patient with a cranial site of interest thereof located in predetermined relation with said X-axis and with said X-ray source and said X-ray film holder;

(h) means within said support housing for inducing controlled rotation to said shaft for moving said elongate support beam, X-ray source and X-ray film holder to accomplish tomographic exposure of said X-ray film; and (i) means for controllably moving said horizontal shaft and thus said X-axis laterally relative to said housing between successive X-ray exposures to achieve selected exposures on said X-ray film representing X-ray cuts of said cranial site of interest.

15. The apparatus of claim 14, wherein said means for controllably rotating said horizontal shaft comprises:

(a) a reversible electric motor;

(b) means coupling said reversible electric motor in rotatable driving relating with said rotatable and laterally movable shaft; and (c) means controlling incremental angular rotation of said rotatable and laterally movable shaft.

16. The apparatus of claim 14, wherein said means for controllably moving said horizontal shaft comprises:

(a) shaft support means located within said support housing and being movable in a direction laterally of the longitudinal axis of said shaft; and (b) shaft support actuator means for selectively imparting lateral movement to said shaft support means and said shaft supported thereby to thus achieve lateral movement of said X-axis being defined by said rotatable and laterally movable shaft.

17. The apparatus of claim 16, wherein said shaft support means comprises:

(a) at least one transverse guide element disposed within said support housing and having guiding and supporting relation with said shaft support means and permitting only lateral linear movement of said shaft support means; and (b) said shaft support actuator means controlling incremental lateral linear movement of said shaft support means to achieve predetermined substantially evenly spaced lateral positioning of said shaft support means and said rotary shaft supported thereby.

18. The apparatus of claim 17, wherein said shaft support actuator means comprises:

an elongate threaded drive element having threaded engagement with said shaft support mans, the threads of said elongate threaded element establishing predetermined incremental lateral movement of said shaft support means upon each revolution thereof.

19. The apparatus of claim 17, wherein said transverse guide element comprises:

(a) a pair of parallel guide rods each being located in a common horizontal plane; and (b) said shaft support element having aligned pairs of bushings thereon, each axially aligned pair of bushings being received in guided relation with one of said parallel guide shafts.

20. The apparatus of claim 15, wherein said means coupling said reversible electric motor to said shaft comprises:

(a) a driven sprocket being disposed in non-rotatable relation with said rotatable and laterally movable shaft and upon rotation thereof, inducing rotation to said rotary and laterally movable shaft and to said elongate support member supported thereby;

(b) a drive sprocket being rotatable by said reversible electric motor; and (c) a drive chain being disposed in interengaging relation with said drive and driven sprockets and upon rotation of said reversible electric motor imparting controlled driving rotation to said driven sprockets and said rotatable and laterally movable shaft.

21. Apparatus for conducting cranial X-ray tomography, comprising:

(a) a housing;

(b) a generally horizontally oriented rotatable and laterally movable shaft having a portion thereof projecting from said housing, the longitudinal axis of said rotatable and laterally movable shaft defining an "X" axis;

(c) means for imparting controlled rotation to said generally horizontally oriented rotatable and laterally movable shaft;

(d) an elongate support beam being fixed to said projecting portion of said generally horizontally oriented rotatable and laterally movable shaft;

(e) an X-ray source and an X-ray film holder being supported for arcuate movement about said generally horizontally oriented and laterally movable shaft by said elongate support beam and being disposed in spaced relation with one another such that an X-ray beam from said X-ray source passes through said "X" axis to said film holder to form a tomographic image on X-ray film supported thereby;

(f) means for fixing the head of a patient at a predetermined static location relative to said housing and for maintaining the patient's head fixed at said predetermined static location during multiple tomographic X-ray exposures of said X-ray film;

(g) means for controllably moving said generally horizontally oriented rotatable and laterally movable shaft laterally relative to aid housing and within a plane coincident with said "X"-axis thus laterally adjusting the center point of arcuate movement of said X-ray source and X-ray film holder between successive tomographic X-ray exposures of said X-ray film; and (h) means for controllably rotating said shaft for pivoting said support arm about said center point while said X-ray source is energized.

22. The apparatus of claim 21, wherein said means for controllably rotating said horizontal rotatable and laterally movable shaft comprises:
 (a) a reversible electric motor;
 (b) means coupling said reversible electric motor in rotatable driving relation with said rotatable and laterally movable shaft; and
 (c) means controlling incremental angular rotation of said rotatable and laterally movable shaft.

23. The apparatus of claim 21, including:
 (a) shaft support means being movable relative to said housing in a direction laterally of the longitudinal axis of said shaft; and
 (b) actuator means for selectively imparting lateral movement to said shaft support means and said shaft rotatably supported thereby to thus achieve lateral movement of said X-axis being defined by said rotatable and laterally movable shaft.

24. The apparatus of claim 23, wherein said shaft support means comprises:
 (a) at least one transverse guide element having guiding and supporting relation with said shaft support means and permitting only lateral linear movement of said shaft support means relative to said housing; and
 (b) said actuator means controlling incremental lateral linear movement of said shaft support means relative to said housing to achieve predetermined substantially evenly spaced lateral positioning of said shaft support mean sand said rotary shaft supported thereby between said successive tomographic X-ray exposures.

25. The apparatus of claim 24, wherein said actuator means comprises:
 an elongate threaded drive element being rotatably supported by said housing and having threaded driving engagement with said shaft support means, the threads of said elongate threaded drive element establishing predetermined incremental lateral movement of said shaft support means upon each revolution of said elongate threaded drive element.

26. The apparatus of claim 24, wherein said at least one transverse guide element comprises:
 (a) a pair of parallel guide rods being fixed to said housing; and
 (b) said shaft support means being a shaft support element having axially aligned pairs of bushings thereon, each axially aligned pair of bushings being received in guided relation with one of said parallel guide rods.

27. The apparatus of claim 22, wherein said means coupling said reversible electric motor to said rotatable and laterally movable shaft comprises:
 (a) a driven sprocket being disposed in non-rotatable relation with said rotatable and laterally movable shaft and upon rotation thereof, inducing rotation to said rotatable and laterally movable shaft and to said elongate support beam being supported thereby;
 (b) a drive sprocket being rotatable by said reversible electric motor; and
 (c) a drive chain being disposed in interengaging relation with said drive and driven sprockets and upon controlled rotation of said reversible electric motor imparting controlled driving rotation to said drive and driven sprockets and said rotatable and laterally movable shaft.

* * * * *